United States Patent [19]

Brauer et al.

[11] Patent Number: 4,572,009
[45] Date of Patent: Feb. 25, 1986

[54] CONNECTOR FOR CORE HOLDER

[75] Inventors: Paul R. Brauer, Tulsa; Thomas J. Barnickel; Gary C. Mast, both of Broken Arrow, all of Okla.

[73] Assignee: Temco, Inc., Tulsa, Okla.

[21] Appl. No.: 621,537

[22] Filed: Jun. 18, 1984

[51] Int. Cl.$^4$ .............................................. G01N 37/00
[52] U.S. Cl. ..................................... 73/864.91; 73/38; 73/49.8
[58] Field of Search ...................... 73/864.91, 38, 153, 73/807, 788, 860, 49.8, 37; 175/58, 226; 138/90; 277/21, 74

[56] References Cited

U.S. PATENT DOCUMENTS

| | | | |
|---|---|---|---|
| 2,493,452 | 1/1950 | Grigg | 138/90 X |
| 2,534,718 | 12/1950 | Leas et al. | 73/38 |
| 2,745,057 | 5/1956 | Dotson | 73/38 X |
| 2,821,680 | 1/1958 | Slusser et al. | 73/38 X |
| 2,982,704 | 5/1961 | Shelton et al. | 73/38 X |
| 3,162,037 | 12/1964 | Hurst | 73/38 |
| 3,199,341 | 8/1965 | Heuer, Jr. et al. | 73/807 |
| 3,262,319 | 7/1966 | Orr, Jr. et al. | 73/38 X |
| 3,371,519 | 3/1968 | Slone et al. | 73/38 |
| 3,451,259 | 6/1969 | McNulty | 138/90 X |
| 3,655,205 | 4/1972 | Petersen | 277/74 X |

FOREIGN PATENT DOCUMENTS

| | | | |
|---|---|---|---|
| 135277 | 2/1961 | U.S.S.R. | 73/38 |
| 750347 | 7/1980 | U.S.S.R. | 73/38 |
| 981507 | 12/1982 | U.S.S.R. | 73/788 |

Primary Examiner—Stewart J. Levy
Assistant Examiner—Tom Noland
Attorney, Agent, or Firm—Head, Johnson & Stevenson

[57] ABSTRACT

This concerns a core holder for a rock core in a resilient sleeve within a hollow housing. Longitudinal and radial forces are applied to the core. Fluid samples can be obtained at selected points along the length around the diameter of the core during injection of fluids therethrough. It concerns a special stem and seal for providing fluid or gas communication from within the resilient sleeve and the exterior of the housing.

6 Claims, 4 Drawing Figures

CONNECTOR FOR CORE HOLDER

CROSS-REFERENCE TO RELATED APPLICATION

This application is related to applicants' co-pending application Ser. No. 621,484 filed June 18, 1984 and entitled "RADIAL CORE HOLDER".

BACKGROUND OF THE INVENTION

1. Field of the Invention

The present invention relates especially to an apparatus for holding a core normally cut from a rock taken from a subterranean formation. The core holder normally contains a hollow housing with a resilient sleeve inside thereof. This present invention concerns a fluid conveying means for a fluid conducted from the interior of the resilient sleeve to the exterior of the housing which is normally made of steel.

2. Background of the Invention

In the oil and gas industry, holes are drilled in the earth to subsurface formations which may be productive of oil, gas or minerals. Frequently cores are cut from formations suspected to contain oil or gas. The core or cut rock, which may be of various sizes, e.g. ¾ inches in length by 4 inches long. For these cores to be of any value they must be analyzed to determine various physical properties of the rock from which it is cut. Such properties are measured for permability, porosity, fluid flow and the like.

SUMMARY OF THE INVENTION

The present invention relates to a core holder which includes a hollow housing, preferably made of high quality steel, having a resilient sleeve therein. The core to be analyzed is inserted into the resilient sleeve. In a preferred embodiment, a fixed plug means closes one end of the sleeve and a second plugs means, movably positioned within the hollow housing, closes the other end. In this embodiment, port means are provided in the walls of the housing and sleeve so that fluid samples and fluid pressures can be obtained from selected points or positions spaced about the core as fluid is injected therethrough from passages which are in the plug means.

The port means preferably includes a hollow tubing affixed to the sleeve and extends through the sleeve and protrudes outwardly into an opening means in the housing. A seal seat in the opening means through which the tubing normally extends is provided. This seat is frustoconical in shape with the base or larger end being nearer the interior of said housing than the other or smaller end of the seat. A seal such as an O-ring is within said seal seat and is held in position by the hollow tubing which is inserted in the opening in the housing. The seal is maintained while the tubing moves radially with respect to the opening in the housing.

DESCRIPTION OF THE DRAWINGS

A better understanding and a fuller description of the present invention will appear in connection with the detailed description of the drawings in which.

DESCRIPTION OF THE PREFERRED EMBODIMENT

Figure 1:
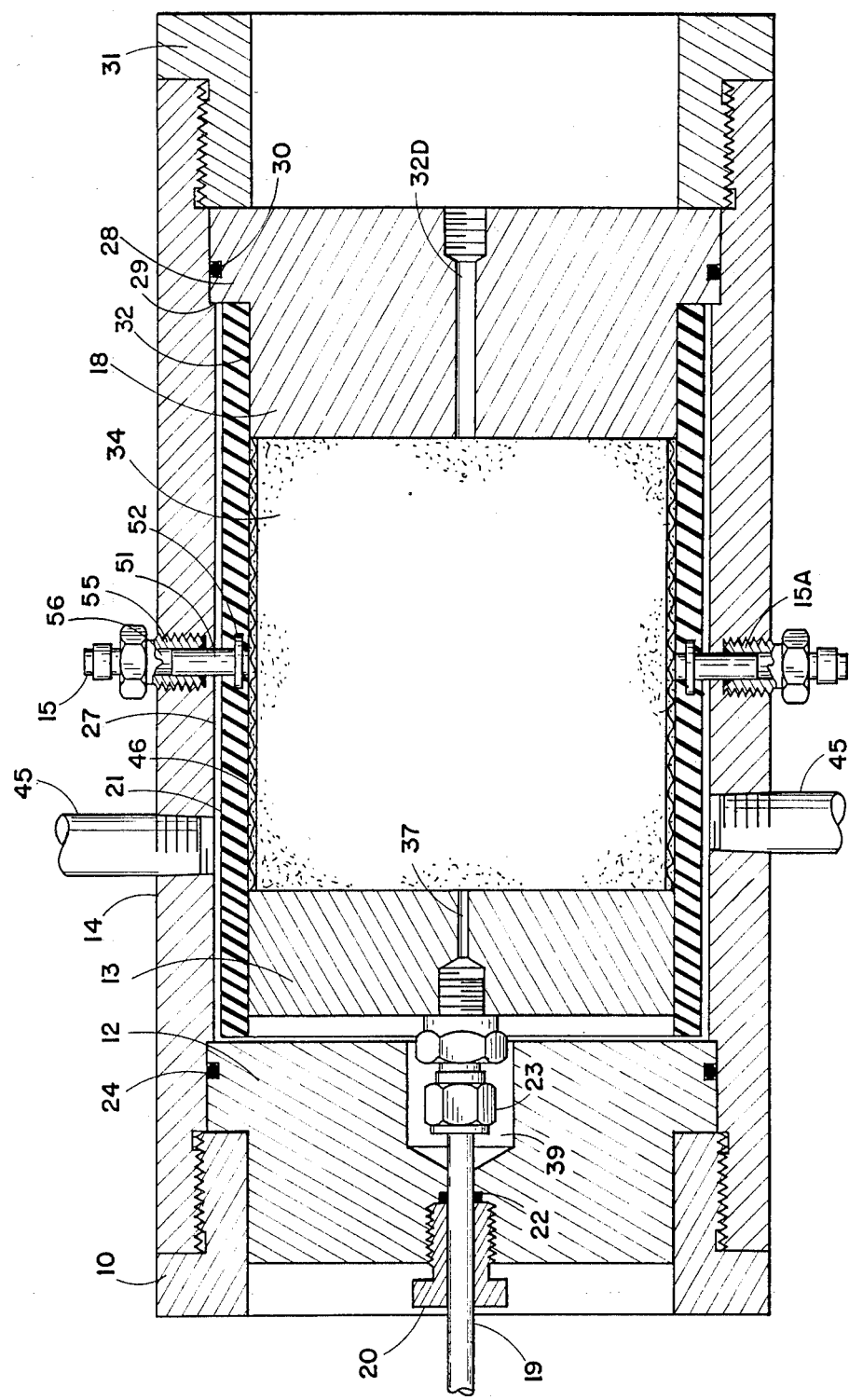
FIG. 1 is a plan view, partly in section of an embodiment of the core holder of this invention indicating the position of the port means which provides fluid communication from the interior of the core to the exterior of the housing.

Reference is first made to FIG. 1 which illustrates a typical core holder which has been modified such that our present invention is made a part thereof. Shown thereon is housing 14 having a central passage 27 in which is mounted sleeve 21. Sleeve 21 can be of any suitable resilient material such as an elastomer. In determining what material to make the sleeve 21 one must determine the pressure, the temperature and chemical composition of the fluids which will be used on the core so that a sleeve may be selected which will withstand such conditions. In one end of housing 14 is a fixed plug means 18. This has a shoulder member 28 which abuts against a shoulder 29 of housing 14. A seal 30 is provided between the plug 18 and the housing. The plug 18 is held in position by end cap 31 which is shown as threadably connected to housing 14.

Mounted within the other end of sleeve 21 is a movable plug 13. Plug 13 is held in by an end plug 12 which is held in position by end cap 10 which is threadably connected to housing 14. Seals 24 are provided between the end plug 12 and the housing. These seals may be O-rings.

Means will now be discussed to that part of the apparatus which permits fluid to be injected through the moving plug 13 to the face of core 34. This includes a tubing 19 which is inserted through plug 20 which is connected by threads to plug 12. Tube 19 extends to a bore within plug 12 into a cavity 39 where it is connected by any suitable seal connector 23 such as a Swagelok SS-400-1-OR to a passage 37 with a movable plug 13. Seals 24 are provided between end plugs 12 and the housing. With this arrangement, as plug 13 moves, tubing 19 can also pass through seals 22 and the connector 23 also moves with the movable plug 13.

There are means provided for applying a radial force on sleeve 21. This includes one or more port means and housing conduits 45 which extends through the wall of the housing. Fluid which, may be either gas or liquid, is applied through conduit means 45 against the outer wall of the sleeve 21 under any selected pressure. In the embodiment shown, fluid from port means 45 also acts on the outer end of movable plug 13 and forces it against the core 34.

Figure 2:
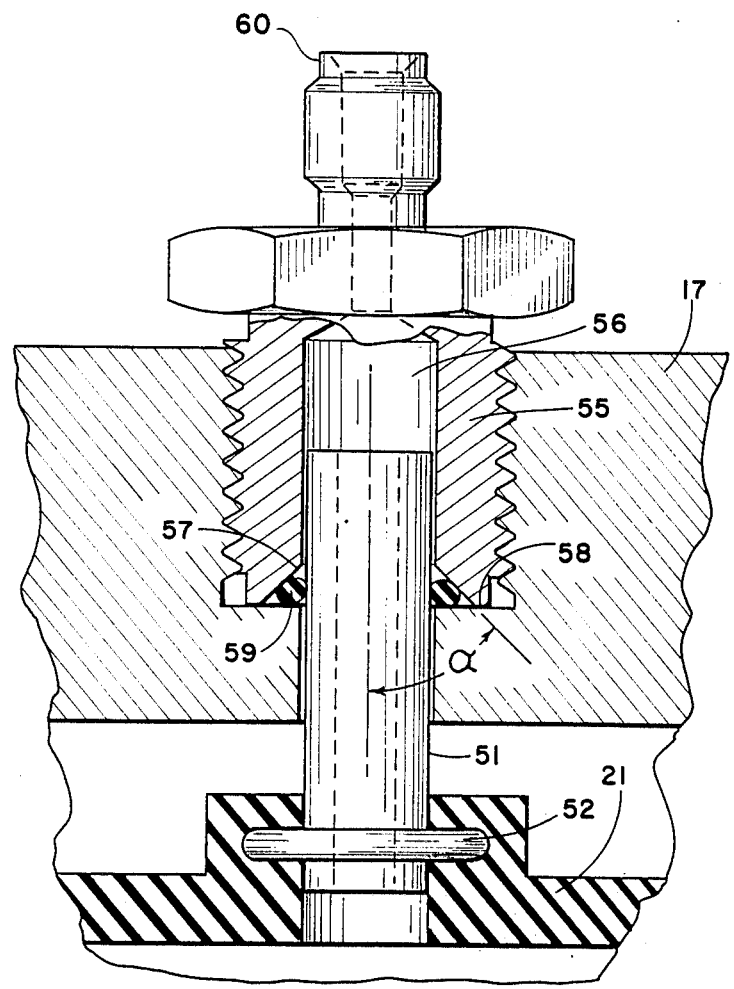
FIG. 2 is an enlarged detailed view showing the seal seat for the seal between the tubing stem embedded in the resilient sleeve and the opening in the housing.

Also shown in FIG. 1 are means 15 and 15A for obtaining fluid samples or pressures or temperatures of the fluid within the core at various radial positions about the core. These port means are novel and form a critical part of the core holder described. A radial tube 51 which has a base 52 is molded into the sleeve 21, has a disc like base 52 which has a plurality of vertical holes 53. A hollow plug 55 having a central passage 56 is screwed into a passage or opening through the wall of housing 14. As shown more clearly in FIG. 2, the lower end of plug 55 has a shoulder 57. It has been found that the shape of this shoulder is most critical in permitting the radial movement of tube 51 while maintaining the seal with the housing and simultaneously permitting a connection to standard tubing at the opposite end 60. This shoulder 57 preferably makes an angle of about 45° with the center line of plug means 55. In the past, we have tried using a shoulder 57 having a face in a plane perpendicular to the longitudinal axis of plug 55. That was found to be ineffective in making the required seal. In the present invention O-ring seal 59 is inserted against seat 57 above the upwardly facing shoulder 58 in the opening of housing 17 into which plug 55 is inserted and is held in position by tube 51 which as indicated in FIG. 1 extends therethrough. Fluid pressure in the annulus between the housing of the resilient sleeve will force the O-ring 59 upwardly. As O-ring 59 is forced upwardly along the upwardly sloping surfaces of the seat, it will be pushed harder against the stem or tube 51. This insures an excellent seal.

Figures 3, 4:
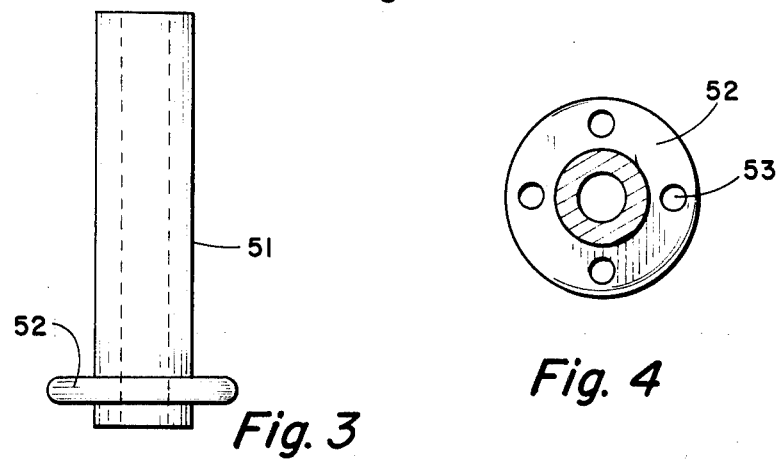
FIG. 3 shows a preferred tubing stem for the port means.
FIG. 4 shows an end view of the stem of FIG. 3.

Attention is next directed to FIG. 3 which shows a tube or stem 51 having a base section 52 which is molded to the sleeve 21 and as shown in FIG. 4 has a plurality of vertical holes 53.

While the invention has been described with a certain degree of particularity, it is manifest that many changes may be made in the details of construction and the arrangement of components without departing from the spirit and scope of this disclosure. It is understood that the invention is not limited to the embodiment set forth herein for purposes of exemplification, but is limited only by the scope of the attached claim or claims, including the full range of equivalency to which each element thereof is entitled.

What is claimed is:

1. In a core holder having a hollow housing and a resilient sleeve thereon the improvement comprising:
    a tubing affixed to said sleeve and extending through said sleeve and protruding outwardly therefrom into, but not through an opening means in said housing in a slidable relation therewith;
    a seal seat in said opening means through which said tubing normally extends, said seat being frusto-conically shaped with its large end being nearer to the interior of said housing than the smaller other end of said seat; and
    a seal within said seal seat through which said tubing movably extends.

2. A core holder as defined in claim 1 in which said tubing has a ring shaped disc attached thereto and molded into said sleeve.

3. A core holder as defined in claim 2 in which said disc is metal with holes therethrough.

4. A core holder as defined in claim 1 in which a face of said seal seat makes an angle of about 45° with the longitudinal axis of the opening through said housing.

5. A core holder comprising:
    a hollow housing having an opening through a wall thereof;
    a resilient sleeve mounted within said housing;
    a tubing fixed to said sleeve with one end extending through said sleeve and the other end protruding outwardly into said opening and movably with respect to any connector connected to the opening of said housing;
    a seal seat in said opening, said seat having a sloping sealing surface, with the ends of such surface each forming a circle, with the circle nearer the interior of the housing being larger than the circle near the outside of the housing;
    a seal in said seal seat and in contact with the outer surface of said tubing;
    means to apply pressure to the interior of said sleeve and the side of said seal nearer said sleeve.

6. A core holder comprising:
    a hollow housing having an opening through a wall thereof, the inner part of said opening being of one diameter and the outer part of said opening being of a larger diameter and being threaded;
    a hollow plug screwable and threadably connectible to the threads of said opening;
    a seal seat on the internal end of said hollow plug, said seat being frusto-conically shaped with its large end being nearer to the interior of said housing than the smaller other end of said seat;
    a tubing fixed to said sleeve with one end and extending through said sleeve, the other end protruding outwardly into said hollow plug but not extending therethrough and being slidable with respect to said opening in said hollow plug; a seal in said seal seat and in contact with the outer surface of said tubing.

* * * * *